United States Patent
Ishida et al.

(10) Patent No.: US 6,570,010 B2
(45) Date of Patent: May 27, 2003

(54) INCLUSION COMPOUNDS OF VANILLYL ALCOHOL DERIVATIVE IN CYCLODEXTRIN AND COMPOSITIONS CONTAINING THE SAME

(75) Inventors: Kenya Ishida, Kanagawa (JP); Satomi Kunieda, Kanagawa (JP); Akira Amano, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 11 days.

(21) Appl. No.: 09/882,251

(22) Filed: Jun. 18, 2001

(65) Prior Publication Data

US 2002/0013235 A1 Jan. 31, 2002

(30) Foreign Application Priority Data

Jun. 20, 2000 (JP) .................................. 2000-184075

(51) Int. Cl.$^7$ .................... C08B 37/16; A61K 31/715; A61K 31/075; C07C 43/20
(52) U.S. Cl. .................... 536/103; 514/58; 514/718; 568/662
(58) Field of Search ..................... 536/103; 514/58, 514/718; 568/662

(56) References Cited

U.S. PATENT DOCUMENTS 5,144,964 A    9/1992   Demain

FOREIGN PATENT DOCUMENTS

| EP | 61-9293 | 3/1986 | ............ C07C/43/23 |
| EP | 0 988 852 A2 | 3/2000 | |
| JP | 61-55889 | 11/1986 | ............ A61K/7/16 |

OTHER PUBLICATIONS

Patent Abstracts sof Japan (May 22, 1982) 57082308.
Patent Abstracts of Japan (Jun. 25, 1987) 62142132.
Patent Abstracts of Japan (Oct. 20, 1998) 10279986.
Patent Abstracts of Japan (Apr. 5, 1984) 59059663.
Patent Abstract of Japan (Sep. 9, 1987) 62205007.
European Search Report dated Jan. 18, 2002.
Galetto, W, et al., "Some Benzyl Ethers in the Extract of Vanilla (Vanilla planifolia)" J. Agric. Food Chem., vol. 26, No. 1, 1978 (195–197).

*Primary Examiner*—Kathleen K. Fonda
(74) *Attorney, Agent, or Firm*—Sughrue Mion, PLLC

(57) ABSTRACT

An inclusion compound, which comprises a cyclodextrin or a branched cyclodextrin and a vanillyl alcohol derivative represented by the following formula (I) having been included therein:

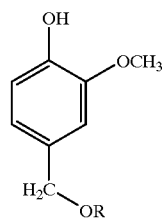

(I)

wherein, R represents a $C_{1-6}$ alkyl group; and a composition containing the same. The inclusion compound exhibits remarkably reduce impure taste of VE and heightens its water solubility and stability. The inclusion compound considerably enhances and prolongs the pungent taste and warm-feeling imparting effect of VE per se and further increase and prolong the cool or refresh-feeling heightening effect of VE per se when used in combination with a refrigerant.

8 Claims, 2 Drawing Sheets

STIMULUS EFFECT OF VBE β-CD INCLUSION COMPOUND

SYNERGISTIC EFFECT OF VBE β-CD INCLUSION COMPOUND AND MENTHOL

INCLUSION COMPOUNDS OF VANILLYL ALCOHOL DERIVATIVE IN CYCLODEXTRIN AND COMPOSITIONS CONTAINING THE SAME

SUMMARY OF THE INVENTION

The present invention relates to inclusion compounds of a vanillyl alcohol derivative (which may hereinafter be abbreviated as "VE"), and compositions containing the same. In particular, the invention pertains to inclusion compounds of VE, as well as compositions containing the same, which has an effect of further enhancing and prolonging the pungent taste and warm-feeling imparting effect (while VE per se has a pungent taste and warm-feeling imparting effect) and has an effect of further increasing and prolonging the cool or refresh-feeling heightening effect when used in combination with a refrigerant (while VE per se has a cool or refresh-feeling heightening effect when used in combination with a refrigerant).

BACKGROUND ART

Ether compounds of vanillyl alcohol are known to exist in the form of a methyl or ethyl ether in vanilla beans as their fragrant component [J. Agric. Food Chem., 26(1), 195 (1978]. It is also known that vanillyl alcohol derivatives represented by the above-described formula (I) have a strong pungent taste and warm-feeling imparting effect (JP-B-61-9293) or are effective for enhancement of the refresh-feeling imparting effect of menthol (JP-B-61-55889) (The term "JP-B" as used herein means an examined Japanese patent publication).

Although these VEs have a strong pungent taste and warm-feeling imparting effect, they are accompanied with the problems that their pungent taste is not pure but contains some bitterness, they require a special care upon handling because of having strong stimulation, their solubility in water is markedly low and they tend to be colored with the passage of time.

An object of the invention is therefore to markedly reduce the impure taste, enhance the water solubility, and enhance the stability of VE. Described specifically, an object of the present invention is to provide a novel inclusion compound of VE which has an effect of further enhancing and prolonging the pungent taste and warm-feeling imparting effect (while VE per se has a pungent taste and warm-feeling imparting effect) and has an effect of further increasing and prolonging the cool or refresh-feeling heightening effect when used in combination with a refrigerant (while VE per se has a cool or refresh-feeling heightening effect when used in combination with a refrigerant), and also markedly reduce the impure taste and water solubility of VE; and compositions containing the same.

SUMMARY OF THE INVENTION

The present inventors have proceeded with various investigations with a view to overcoming the above-described problems. As a result, it has been found that inclusion of VE in a cyclodextrin (which may hereinafter be abbreviated as "CD") makes it possible to markedly reduce the impure taste of VE and heighten its water solubility and at the same time, to further enhance and prolong the pungent taste and warm-feeling imparting effect (while VE per se has a pungent taste and warm-feeling imparting effect) and to further increase and prolong the cool or refresh-feeling heightening effect when used in combination with a refrigerant (while VE per se has a cool or refresh-feeling heightening effect when used in combination with a refrigerant), leading to completion of the invention. The invention embraces each of the following embodiments of the invention.

(1) An inclusion compound which comprises a cyclodextrin or a branched cyclodextrin and a vanillyl alcohol derivative represented by the following formula (I) having been included therein:

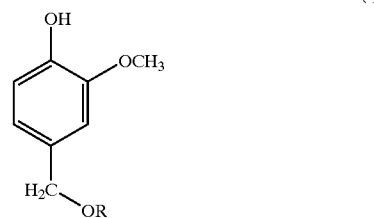

(I)

wherein, R represents a $C_{1-6}$ alkyl group.

(2) The inclusion compound according to the above-described item (1), wherein the vanillyl alcohol derivative represented by the formula (I) is vanillyl-n-butyl ether.

(3) The inclusion compound according to the above-described item (1), wherein the cyclodextrin is β-cyclodextrin.

(4) The inclusion compound according to item (2), wherein the cyclodextrin is β-cyclodextrin.

(5) A composition which comprises the inclusion compound according to item (1).

(6) A composition which comprises the inclusion compound according to item (2).

(7) A composition which comprises the inclusion compound according to item (3).

(8) A composition which comprises the inclusion compound according to item (4).

DETAILED DESCRIPTION OF THE INVENTION

Figure 1A:
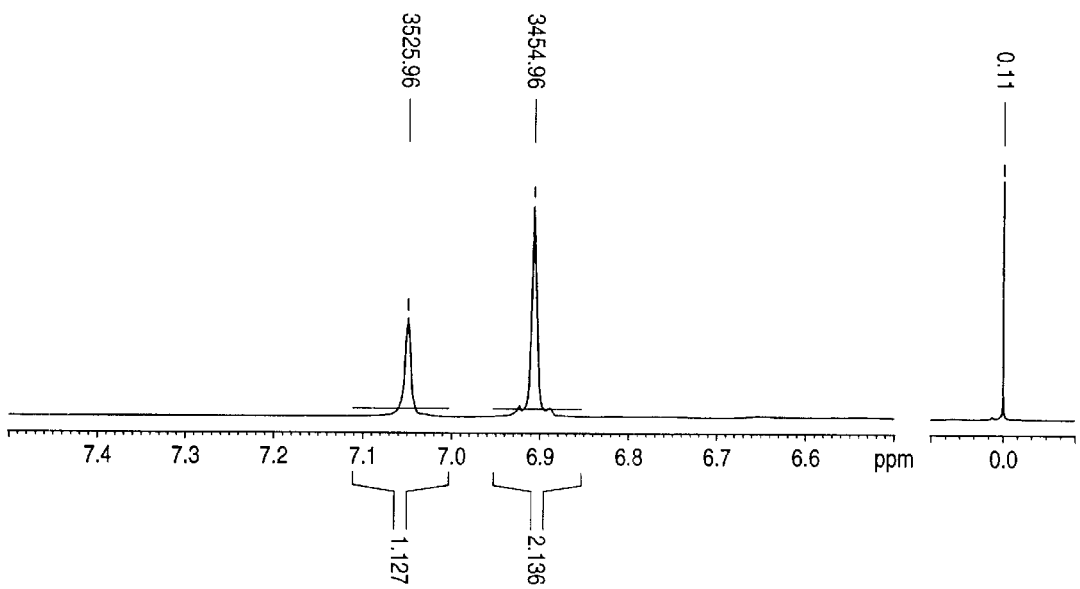
FIG. 1A is a $^1$H-NMR spectrum of the aromatic ring portion of vanillyl-n-butyl ether and FIG. 1B is that of the inclusion compound of vanillyl-n-butyl ether in β-CD obtained in Example 1.

The present invention will hereinafter be described more specifically.

The term "inclusion compound" or "clathrate compound" as used herein means a compound wherein a host molecule forms a basket-like crystal lattice and a guest molecule is included (enclosed) in the cavities of the lattice under appropriate conditions.

Examples of the CD usable in the present invention include non-branched CDs such as α-CD, β-CD and γ-CD;

branched CDs wherein one molecule or two molecules of one or more oligosaccharide(s) such as glucose, maltose or maltotriose has(have) been bonded to the non-branced CDs (α-1,6 bond); and branched CDs wherein 3 to 8 molecules of a hydroxypropyl group have been bonded to non-branched CDs by the addition of propylene oxide. The CD to which one glucose molecule has been bonded will be called "glucosyl CD (which will hereinafter be described as "G1-CD"), the CD to which two glucose molecules have been bonded will be called "diglucosyl CD (which will hereinafter be described as "G1-G1-CD"), the CD to which one maltose molecule has been bonded will be called "maltosyl CD (which will hereinafter be described as "G2-CD"), the CD to which two maltose molecules have been bonded will be called "dimaltosyl CD (which will hereinafter be described as "G2-G2-CD"), and the CD to which 3 to 8 hydroxypropyl groups have been bonded will be called "hydroxypropyl CD" (which will hereinafter be described as "HP-CD"). Preferred examples of the CD in the invention include β-CD, branched β-CDs such as G1-β-CD and G2-β-CD, and γ-CD. These CDs may be used either singly or in combination.

The inclusion compound of the invention is prepared by allowing VE into contact with CD in the presence of water, thereby forming an inclusion compound of VE in CD. The resulting inclusion compound is provided as a product as is, that is, in the form of an aqueous solution, or after filtering the precipitate and then drying, or drying and pulverizing if desired. The contact is usually conducted by dissolving CD in water, adding VE to the resulting solution, and stirring or shaking the mixture vigorously for several seconds to several hours in a stirrer or homogenizer. Alternatively, shaking in a hermetically sealed container or inclusion of VE by ultrasonic treatment can be employed. VE can be added as is or after dissolving in a suitable organic solvent.

Examples of the organic solvent usable in the invention include acetone, ethanol, methanol, isopropanol and tetrahydrofuran. No particular limitation is imposed on the amount of the organic solvent insofar as it permits dissolution of VE therein. The amount of VE is usually 0.1 to 1 mole, preferably 0.5 to 1.0 mole per mole of CD. The reaction temperature upon contact is usually 0 to 70° C., preferably 5 to 60° C.

The inclusion compound prepared in the above-described manner can be dried as is and pulverized into the inclusion compound powder containing VE.

The compound of the invention forms a clathrate, which can be confirmed by the measurement using nuclear magnetic resonance (NMR).

The inclusion compound of VE in CD available by the invention can be used in various forms, for example, as powder or as a solution.

The inclusion compound of VE in CD obtained by the present invention stably exists in the form of a powder and therefore can be made into a composition by mixing it with various types of powders. Examples of the powders which can be mixed with the clathrate compound of the present invention include powdery fragrances, powdery extracts, powdery warm-feeling imparting agents, powdery cool-feeling imparting agents, inorganic salts, surfactants, saccharides, organic salts, medicinal components, antibacterial agents, antifungal agents, nutrient agents, enzymes, polymers, dyes, pigments, abrasives, antioxidants, antiseptics, deodorants, solid paraffin, and the like.

The inclusion compound of VE in CD obtained by the present invention is stable in aqueous solutions and therefore can be made into an aqueous composition by mixing it with various types of water-soluble components. Examples of the water-soluble components which can be mixed with the clathrate compound of the present invention include water-soluble fragrances, extracts, warm-feeling imparting agents, cool-feeling imparting agents, inorganic salts, surfactants, saccharides, organic salts, medicinal components, antibacterial agents, antifungal agents, nutrient agents, enzymes, polymers, dyes, pigments, abrasives, antioxidants, antiseptics, deodorants, protic organic solvents, and the like.

By using the resulting powdery composition or aqueous composition containing the inclusion compound of VE in CD, the following products may be manufactured in a manner similar to the inclusion compound of VE in CD alone.

The application range or method of the inclusion compound of VE in CD and compositions containing the compounds available by the invention must be changed as needed depending on the kind of the product to which they are applied or using purpose. It is usually preferred to add the inclusion compound of VE in CD in an amount of 0.00001 to 10 wt. %, particularly 0.001 to 5 wt. % based on the whole composition of the product to which they are applied. To the product to which they are applied, any components that have the effects depending on its using purpose can be added as needed and then, the product is provided as oral care compositions, skin preparations for external use, bathing preparations, foods and drinks, fragrant cosmetics, sanitary materials, and pharmaceuticals etc.

Examples of the product to which the inclusion compound of VE in CD and compositions containing the compounds can be incorporated include softening lotion, astringent, cleansing lotion, milky lotion, systemic lotion, after-shave lotion or gel, massage cream, cleansing cream or gel, warm-feeling imparting or cool-feeling imparting cataplasm, shampoo, conditioner, perfume, colon, hair cosmetics such as hair tonic, hair cream and hair growth promoting lotion, liquid or powder or solid bathing composition, soap, detergent, softener, deodorizer, dental paste, mouth wash, ointment, soft drink, tonic, gum, candy, throat candy, confectioneries, medicated cream, medicated jel, and the like. Above all, the inclusion compound of the invention is suited in use for oil-in-water type preparations composed mainly of water such as systemic lotion, mouth wash, shampoo and hair tonic and preparations dissolved in water such as bathing composition. In addition, the inclusion compound of VE in CD obtained by the present invention hardly vaporize in comparison with the VE which is not in the form of clathrate. Accordingly, the inclusion compound of VE in CD of the present invention may be preferably used in the products which are produced by heat treatment, such as baked confectioneries.

The inclusion compound of the invention can also be used in combination with another warm-feeling imparting agent such as pepper powder, pepper tincture, pepper extract, capsaicin, nonylic acid vanillyl amide, or allyl isothiocyanate. By the use in combination with a cool-feeling imparting agent such as 1-menthol, 1-isopregol, 3-(1-menthoxy) propane-1,2-diol, paramenthane-3,8-diol, 3-(1-menthoxy)-2-methylpropane-1,2-diol, 3-(1-menthoxy)propane-1-ol, 3-(1-menthoxy)butan-1-ol or peppermint oil, its cool-feeling or refresh-feeling imparting effect can be heightened or allowed to last long. The inclusion compound used in combination with such a warm-feeling or cool-feeling imparting agent can be provided as oral care compositions, skin preparations for external use, bathing preparations, foods and drinks, fragrant cosmetics, sanitation materials, or pharmaceuticals etc., as exemplified above.

The present invention includes the compound, compositions, methods and others described below:

1. An inclusion compound which comprises a cyclodextrin or a branched cyclodextrin and a vanillyl alcohol derivative represented by the following formula (I) having been included therein:

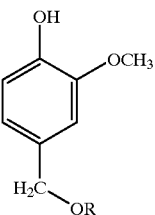

(I)

wherein, R represents a $C_{1-6}$ alkyl group.

2. The inclusion compound according to 1 above, wherein the vanillyl alcohol derivative represented by the formula (I) is vanillyl-n-butyl ether.
3. A composition comprising the inclusion compound according to 1 above.
4. The method for improving taste of a vanillyl alcohol derivative, which comprises enclosing the vanillyl alcohol derivative in a cyclodextrin or a branched cyclodextrin.
5. A refrigerant comprising the inclusion compound and menthol.
6. An oral care composition comprising the inclusion compound in an amount of 0.00001 to 10 wt. %.
7. A skin preparation for external use, which comprises the inclusion compound in an amount of 0.00001 to 10 wt. %.
8. A bathing preparation, which comprises the inclusion compound in an amount of 0.00001 to 10 wt. %.
9. A food or beverage, which comprises the inclusion compound in an amount of 0.00001 to 10 wt. %.
10. A method for preparing an inclusion compound of a vanillyl alcohol derivative, which comprises adding, to a 1 to 50 wt. % aqueous solution of the cyclodextrin or branched cyclodextrin, 0.1 to 1 mole of the vanillyl alcohol derivative per mole of the cyclodextrin or branched cyclodextrin.

The present invention will hereinafter be described in further details by Examples and Tests. It should however be borne in mind that the present invention is not limited to or by them.

The following apparatuses were used for each measurement.

Nuclear magnetic resonance spectrum: $^1$H-NMR: AM-400 (400 MHz) (trade name; product of Bruker)

External standard substance: tetramethylsilane

Ultraviolet absorption spectrum (V): UV-260 (trade name; product of Shimadzu Corp.)

EXAMPLE 1

Preparation of Inclusion Compound of Vanillyl-n-butyl Ether in β-CD

In 300 ml of water was dissolved 22.7 g (0.02 mol) of β-CD (product of NIHON SHOKUHIN KAKO Co., Ltd.) at 60° C. under stirring. To the resulting solution was added 4.2 g (0.02 mol) of vanillyl-n-butyl ether (product of Takasago International Corporation). After stirring at the same temperature for about 1 hour, the reaction mixture was cooled. The crystals thus precipitated were collected by filtration at 5° C., washed with water and then lyophilized, whereby 22.0 g of the target inclusion compound of vanillyl-n-butyl ether in β-CD was obtained as white powder.

The proton nuclear magnetic resonance spectrum ($^1$H-NMR) [solvent=deuterated dimethylsulfoxide: $(CD_3)_2SO$] of the resulting inclusion compound and ultraviolet absorption spectrum (279 nm) of its aqueous solution were measured, whereby the compound was confirmed to be an about 1:0.79 (molar ratio) compound of β-CD and vanillyl-n-butyl-ether (128 mg of vanillyl-n-butyl ether was contained in 1000 mg).

Figure 1B:
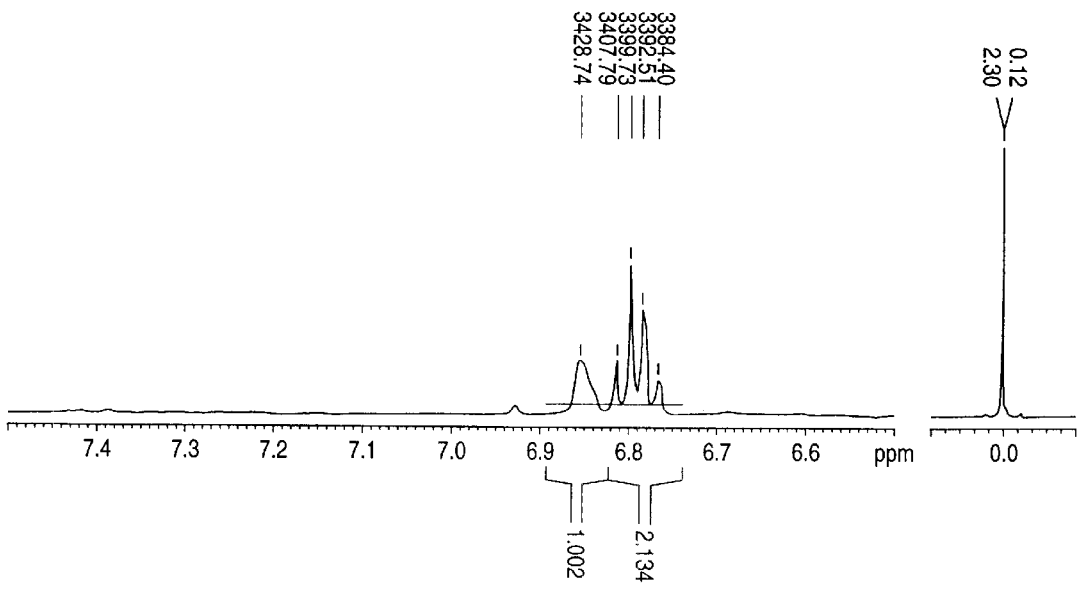

In order to confirm that the compound is not a simple mixture but forms a clathrate, it was subjected to $^1$H-NMR analysis. FIG. 1A shows $^1$H-NMR spectrum ($D_2O$ solution) of the aromatic ring portion of vanillyl-n-butyl ether as measured with tetramethylsilane (TMS) as an external standard. FIG. 1B shows $^1$H-NMR spectrum ($D_2O$ solution) of the vanillyl-n-butyl ether aromatic ring portion of the invention compound, that is, inclusion compound of vanillyl-n-butyl ether in β-CD as measured with tetramethylsilane (TMS) as an external standard. The difference in spectrum between A and B results from the inclusion by β-CD (refer to FIG. 1). Measurement of $^1$H-NMR of the extract of the included substance from an aqueous solution of this inclusion compound by using an organic solvent showed that it exhibited a similar spectrum pattern to vanillyl-n-butyl ether. From this finding, it has been confirmed that vanillyl-n-butyl ether was enclosed with the inclusion compound without decomposition.

EXAMPLE 2

Preparation of Inclusion Compound of Vanillyl-n-butyl Ether in G1-β-CD

In 15 ml of water was dissolved 3.89 g (3.0 mmol) of G1-β-CD (product of Ensuiko Sugar Refining Co., Ltd.) under stirring. To the resulting solution was added a solution of 567 mg (2.7 mmol, 0.9 mol equivalent, 14.6 wt. % relative to CD) of vanillyl-n-butyl ether dissolved in 10 ml of acetone. After stirring at 35° C. for about 1 hour, acetone was distilled off under reduced pressure to yield a transparent solution. The resulting solution was lyophilized, whereby 4.40 g of a dry white inclusion compound was obtained. Ultraviolet absorption spectrum (279 nm) for measuring the content of vanillyl-n-butyl ether in the inclusion compound by using its aqueous solution revealed that it was an about 1:0.104 (weight ratio) inclusion compound (104 mg of vanillyl-n-butyl ether was contained in 1000 mg).

EXAMPLE 3

Preparation of Inclusion Compound of Vanillyl-n-butyl Ether in γ-CD

In 52 ml of water was dissolved 12.9 g (10 mmol) of γ-CD (product of Ensuiko Sugar Refining Co., Ltd.) at 30° C. under stirring. To the resulting solution was added 1.89 g (9 mmol, 0.9 mol equivalent, 14.65 wt. % relative to CD) of vanillyl-n-butyl ether (product of Takasago International Corporation). After stirring, at the same temperature for about 1 hour, the white suspension thus obtained by the addition of vanillyl-n-butyl ether was lyophilized, whereby 13.7 g of the target inclusion compound of vanillyl-n-butyl ether in γ-CD was obtained as a white powder. Ultraviolet absorption spectrum (279 nm) for measuring the content of vanillyl-n-butyl ether in the inclusion compound by using its aqueous solution revealed that it was an about 1:0.120 (weight ratio) inclusion compound (120 mg of vanillyl-n-butyl ether was contained in 1000 mg).

Solubility (wt. %) of each of the inclusion compounds obtained in the above-described Examples in water of 20° C. is shown in Table 1. In this table, vanillyl-n-butyl ether will be abbreviated as VBE.

It has been confirmed, as shown in the below-described table, that water solubility increased by 10 to 1000 times by inclusion.

TABLE 1

|  | Solubility of inclusion VBE in terms of compound concentration | Solubility of |
| --- | --- | --- |
| VBE |  | <0.002% |
| Inclusion compound of vanillyl-n-butyl ether in β-CD prepared in Example 1 | >0.27% | >0.036% |
| Inclusion compound of vanillyl-n-butyl ether in G1-β-CD prepared in Example 2 | >20% | >2% |
| Inclusion compound of vanillyl-n-butyl ether in γ-CD prepared in Example 3 | >0.18% | >0.021% |

EXAMPLE 4

Sensory Evaluation Test

In a 100-ml measuring flask was charged 0.78 g (containing 0.1 g of vanillyl-n-butyl ether) of the inclusion compound of vanillyl-n-butyl ether in β-CD prepared in Example 1. It was dissolved in ethanol to give a total volume of 100 ml. In a 1000-ml measuring flask, 1 ml of the resulting solution was charged and added with distilled water to give a total volume of 1000 ml.

COMPARATIVE EXAMPLE 1

For comparison, in a 100-ml measuring flask was charged 0.1 g of vanillyl-n-butyl ether. It was dissolved in ethanol to give a total volume of 100 ml. In a 1000-ml measuring flask, 1 ml of the resulting solution was charged, followed by the addition of 1 ml of a 0.68% aqueous solution of β-CD. Distilled water was added to give a total volume of 1000 ml.

TEST EXAMPLE 1

With regards to the aqueous solution of the inclusion compound of vanillyl-n-butyl ether in β-CD prepared in Example 4 and the aqueous solution of vanillyl-n-butyl ether and β-CD prepared in Comparative Example 1, warm feeling and stimulus were evaluated.

Figure 2:
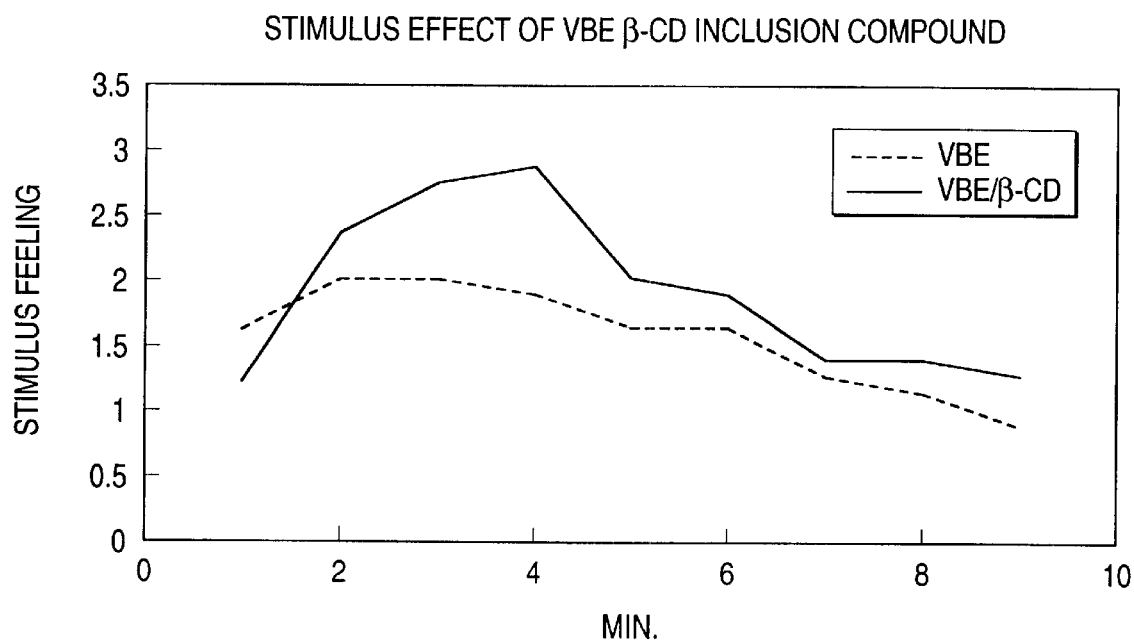
FIG. 2 is a graph illustrating evaluation results of warm feeling and stimulus of the aqueous solution of inclusion compound of vanillyl-n-butyl ether in β-CD obtained in Example 4 and aqueous solution of VBE and β-CD obtained in Comparative Example 1.

A panel of 8 experts having an experience of at least 5 years held 10 ml of each of the above-described aqueous solutions in their mouth for 20 seconds and after discharging, evaluated its warm feeling and strength of the stimulus with the passage of time by 7-stage ranking system. They were evaluated based on an average of the scores of eight experts. Results are shown in FIG. 2.

From Test Example 1, it has been found that the inclusion compound of vanillyl-n-butyl ether in β-CD showed immediate and long-lasting warm feeling or stimulus, which are more excellent than vanillyl-n-butyl ether not in the form of an inclusion compound. The compound was proved to be an inclusion compound because effects were not available from a simple mixture of vanillyl-n-butyl ether and β-CD.

EXAMPLE 5

In a 100-ml of a measuring flask were charged 0.9 g of 1-menthol (product of Takasago International Corporation) and 0.78 g (containing 0.1 g of vanillyl-n-butyl ether) of the inclusion compound of vanillyl-n-butyl ether in β-CD prepared in Example 1. They were dissolved in ethanol to give a total volume of 100 ml. In a 1000-ml measuring flask was charged 1 ml of the resulting solution, followed by the addition of distilled water to give a total volume of 1000 ml.

COMPARATIVE EXAMPLE 2

For comparison, in a 100-ml of a measuring flask were charged 0.9 g of 1-menthol and 0.1 g of vanillyl-n-butyl ether. They were dissolved in ethanol to give a total volume of 100 ml. In a 1000-ml measuring flask was charged 1 ml of the resulting solution, followed by the addition of distilled water to give a total volume of 1000 ml.

TEST EXAMPLE 2

Figure 3:
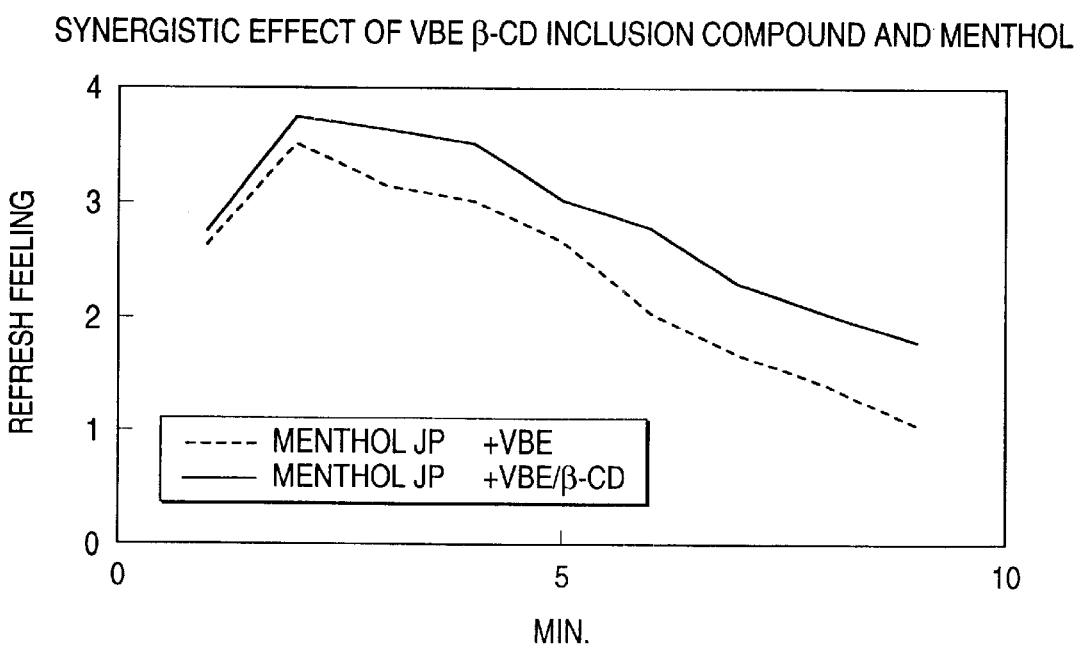
FIG. 3 is a graph illustrating evaluation results of cool or refresh feeling of the aqueous solution of 1-menthol and inclusion compound of vanillyl-n-butyl ether in β-CD obtained in Example 5 and aqueous solution of 1-menthol and VBE obtained in Comparative Example 2.

With regards to the aqueous solution of 1-menthol and the inclusion compound of vanillyl-n-butyl ether in β-CD obtained in Example 5 and the aqueous solution of 1-menthol and vanillyl-n-butyl ether obtained in Comparative Example 2, the cool or refresh feeling imparted by them was evaluated in a similar manner to Test Example 1. The results are shown in FIG. 3.

From Test Example 2, it has been found that cool or refresh feeling was imparted immediately and durability of this effect was excellent when the inclusion compound of vanillyl-n-butyl ether in β-CD was used in combination with menthol, compared with the combined use of menthol with vanillyl-n-butyl ether not in the form of an inclusion compound.

TEST EXAMPLE 3

Evaluation of Impure Taste

With regards to the aqueous solution of the inclusion compound of vanillyl-n-butyl ether in β-CD prepared in Example 4 and the aqueous solution of vanillyl-n-butyl ether and β-CD prepared in Comparative Example 1, impure taste was evaluated. As in Test Example 1, evaluation was conducted by a panel of 8 experts who were asked to compare the strength of the taste just after they held each of the aqueous solutions in their mouth.

From the results of Table 2, it has been confirmed that impure taste of the inclusion compound of the invention was markedly alleviated compared with vanillyl-n-butyl ether not in the form of an inclusion compound.

TABLE 2

| Evaluation items of impure taste | The number of experts who answered Example 4 was stronger | The number of experts who answered Comparative Example 1 was stronger | The number of experts who did not recognize their difference |
| --- | --- | --- | --- |
| Astringent taste | 0 | 8 | 0 |
| Sweet taste | 0 | 7 | 1 |

EXAMPLE 6

Chewing Gum

The inclusion compound of vanillyl-n-butyl ether in β-CD prepared in Example 1 was mixed in a conventional manner in accordance with the below-described formulation, whereby 100 g of a chewing gum was prepared.

TABLE 3

| Components | Mixing ratio (wt. %) |
| --- | --- |
| Inclusion compound of vanillyl-n-butyl ether in β-CD prepared in Example 1 | 0.1 |
| Mint flavor | 1.0 |
| Thick malt syrup | 13.0 |
| Gum-base resin | 20.0 |
| Powder sugar | Balance |

EXAMPLE 7

Dental Paste

The inclusion compound of vanillyl-n-butyl ether in β-CD prepared in Example 1 was mixed in a conventional manner in accordance with the formulation shown in Table 4, whereby 100 g of a dental paste was prepared.

| Component | Mixing ratio (wt. %) |
| --- | --- |
| Inclusion compound of vanillyl-n-butyl ether in β-CD prepared in Example 1 | 0.037 |
| 1-Menthol | 0.5 |
| Calcium hydrogenphosphate (dihydrate) | 50.0 |
| Glycerin | 25.0 |
| Sodium lauryl sulfate | 1.4 |
| Carboxymethylcellulose sodium | 1.5 |
| Saccharin sodium | 0.15 |
| Sodium benzoate | 0.05 |
| Flavor | 0.1 |
| Purified water | Balance |

EXAMPLE 8

Carbonated Beverage

A carbonated beverage was prepared, in accordance with the formulation shown in Table 5, by using the inclusion compound of vanillyl-n-butyl ether in β-CD prepared in Example 1.

TABLE 5

| Component | Mixing ratio (wt. %) |
| --- | --- |
| Lemon juice concentrate | 0.45 |
| Liquid sugar (fruit sugar dextrose) | 12.9 |
| Lemon flavor | 0.1 |
| Inclusion compound of vanillyl-n-butyl ether in β-CD prepared in Example 1 | 0.0074 |
| Water | 20.0 |
| Aerated water | Balance |

EXAMPLE 9

Vitamin-containing Tonic

A vitamin-containing tonic was prepared, in a conventional manner in accordance with the formulation shown in Table 6, by using the inclusion compound of vanillyl-n-butyl ether in β-CD prepared in Example 1.

TABLE 6

| Component | Mixing ratio (wt. %) |
| --- | --- |
| Fruit sugar dextrose liquid sugar | 26.0 |
| Honey | 1.0 |
| Citric acid | 0.72 |
| Vitamin $B_2$ phosphate ester sodium | 0.005 |
| Vitamin $B_6$ | 0.005 |
| Nicotinic acid amide | 0.02 |
| Vitamin $B_1$ nitrate salt | 0.005 |
| Inositol | 0.05 |
| Green tea extract | 0.05 |
| Inclusion compound of vanillyl-n-butyl ether in β-CD prepared in Example 1 | 0.008 |
| Flavor | 0.12 |
| Water | Balance |

EXAMPLE 10

Bathing Composition

The inclusion compound of vanillyl-n-butyl ether in β-CD prepared in Example 1 was mixed in a conventional manner in accordance with the formulation shown in Table 7, whereby 100 g of a bathing composition was prepared.

TABLE 7

| Component | Mixing ratio (wt. %) |
| --- | --- |
| Inclusion compound of vanillyl-n-butyl ether in β-CD prepared in Example 1 | 0.5 |
| Sodium chloride | 10.0 |
| Silicic anhydride | 0.5 |
| Coloring matter | 0.001 |
| Perfume | 0.1 |
| Neutral anhydrous sodium sulfate | Balance |

EXAMPLE 11

Hair Lotion

The inclusion compound of vanillyl-n-butyl ether in G1-β-CD prepared in Example 2 was mixed in a conventional manner in accordance with the formulation shown in Table 8, whereby 100 g of a hair lotion was prepared.

TABLE 8

| Component | Mixing ratio (wt. %) |
| --- | --- |
| Inclusion compound of vanillyl-n-butyl ether in G1-β-CD prepared in Example 2 | 2.0 |
| β-Glycyrrhetic acid | 0.2 |
| 1-Menthol | 0.1 |
| Polyoxyethylene hydrogenated castor oil | 5.0 |
| BHT (2,6-di-t-butyl-4-methylphenol) | 0.03 |
| Perfume | 0.05 |
| Purified water | Balance |

EXAMPLE 12

Mouth Wash

The inclusion compound of vanillyl-n-butyl ether in β-CD prepared in Example 1 was mixed in a conventional manner in accordance with the formulation shown in Table 9, whereby 100 g of a mouth wash was prepared.

TABLE 9

| Component | Mixing ratio (wt. %) |
| --- | --- |
| Inclusion compound of vanillyl-n-butyl ether in β-CD prepared in Example 1 | 1.0 |
| Ethanol | 12.5 |
| Sodium lauryl sulfate | 1.25 |
| Glycerin | 10.0 |
| 1-Menthol | 0.1 |
| Saccharin | 0.001 |
| Coloring matter | 0.003 |
| Flavor | 0.05 |
| Purified water | Balance |

EXAMPLE 13
Lotion

The inclusion compound of vanillyl-n-butyl ether in γ-CD prepared in Example 3 was mixed in a conventional manner in accordance with the formulation shown in Table 10, whereby 100 g of a lotion was prepared.

TABLE 10

| Component | Mixing ratio (wt.%) |
| --- | --- |
| Inclusion compound of vanillyl-n-butyl ether in γ-CD prepared in Example 3 | 1.0 |
| Loofah extract | 2.0 |
| 1,3-Butyleneglycol | 5.0 |
| Sodium citrate | 0.1 |
| Ethanol | 15.0 |
| Coloring matter | 0.0005 |
| Perfume | 0.05 |
| Purified water | Balance |

EXAMPLE 14
Shampoo

The inclusion compound of vanillyl-n-butyl ether in β-CD prepared in Example 1 was mixed in a conventional manner in accordance with the formulation shown in Table 11, whereby 100 g of a shampoo composition was prepared.

TABLE 11

| Component | Mixing ratio (wt. %) |
| --- | --- |
| Inclusion compound of vanillyl-n-butyl ether in β-CD prepared in Example 1 | 1.0 |
| Decanoic acid | 0.05 |
| Triethanolamine lauryl sulfate | 18.5 |
| 1% aqueous solution of hydroxypropylmethylcellulose | 15.0 |
| Ammonium lauryl sulfate | 8.0 |
| Cocamide | 4.0 |
| Palmitic acid | 0.3 |
| 1,3-dimethylol-5,5-dimethylhydantoin | 0.15 |
| Disodium ethylenediaminetetraacetate | 0.05 |
| Citric acid | 0.03 |
| Sodium chloride | 0.02 |
| Perfume | 0.07 |
| Purified water | Balance |

As described above, the novel inclusion compounds of a vanillyl alcohol derivative (VE) in a cyclodextrin and compositions containing the same, each according to the invention, exhibit marked effects for remarkably reducing impure taste of VE, and heightening its water solubility and stability and at the same time, considerably enhance and prolong the pungent taste and warm-feeling imparting effect (while VE per se has a pungent taste and warm-feeling imparting effect) and further increase and prolong the cool or refresh-feeling heightening effect when used in combination with a refrigerant (while VE per se has a cool or refresh-feeling heightening effect when used in combination with a refrigerant). By application of the invention compound to oral care compositions, skin preparations for external use, bathing preparations, foods and drinks, fragrant cosmetics, sanitation materials or pharmaceuticals etc., their effects or application range can be improved markedly.

While the invention has been described in detail and with reference to specific embodiments thereof, it will be apparent to one skilled in the art that various changes and modifications can be made therein without departing from the spirit and scope thereof.

This application is based on Japanese patent applications no. 2000-184075 filed on Jun. 20, 2000, the entire contents thereof being hereby incorporated by reference.

What is claimed is:

1. An inclusion compound which comprises a cyclodextrin or a branched cyclodextrin and a vanillyl alcohol derivative represented by the following formula (I) having been included therein:

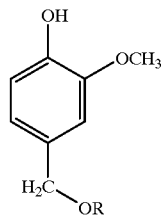

(I)

wherein, R represents a $C_{1-6}$ alkyl group.

2. The inclusion compound according to claim 1, wherein the vanillyl alcohol derivative represented by the formula (I) is vanillyl-n-butyl ether.

3. The inclusion compound according to claim 1, wherein the cyclodextrin is β-cyclodextrin.

4. The inclusion compound according to claim 2, wherein the cyclodextrin is β-cyclodextrin.

5. A composition which comprises the inclusion compound according to claim 1 in combination with a powder, a water soluble component or both a powder and a water soluble component.

6. A composition which comprises the inclusion compound according to claim 2 in combination with a powder, a water soluble component or both a powder and a water soluble component.

7. A composition which comprises the inclusion compound according to claim 3 in combination with a powder, a water soluble component or both a powder and a water soluble component.

8. A composition which comprises the inclusion compound according to claim 4 in combination with a powder, a water soluble component or both a powder and a water soluble component.

* * * * *